United States Patent [19]

Wiktor

[11] Patent Number: 4,681,110
[45] Date of Patent: Jul. 21, 1987

[54] CATHETER ARRANGEMENT HAVING A BLOOD VESSEL LINER, AND METHOD OF USING IT

[76] Inventor: Dominik M. Wiktor, 4 Culin Dr., Cranford, N.J. 07016

[21] Appl. No.: 803,304

[22] Filed: Dec. 2, 1985

[51] Int. Cl.⁴ .......................................... A61M 27/00
[52] U.S. Cl. .................................. 128/343; 128/325
[58] Field of Search ............................. 128/341–345, 128/325, 348.1, 1 R, 759

[56] References Cited

U.S. PATENT DOCUMENTS

| | | | |
|---|---|---|---|
| 4,023,559 | 5/1977 | Gaskell | 128/759 |
| 4,140,126 | 2/1979 | Choudhury | 128/325 |
| 4,503,569 | 3/1985 | Dotter | 128/325 X |
| 4,512,338 | 4/1985 | Balko et al. | 128/341 X |
| 4,545,390 | 10/1985 | Leary | 128/772 |
| 4,562,596 | 1/1986 | Kornberg | 128/325 X |
| 4,577,631 | 3/1986 | Kreamer | 128/325 X |

FOREIGN PATENT DOCUMENTS 1205743  9/1970  United Kingdom ............... 128/343

*Primary Examiner*—Dalton L. Truluck
*Attorney, Agent, or Firm*—Alan H. Levine

[57] ABSTRACT

A catheter arrangement including a main tubing containing a radially expandable liner and a member for moving the liner out of the tubing while the tubing is in a blood vessel. Once out of the tubing, the liner expands radially outwardly into engagement with the blood vessel wall. The liner is a tube of woven plastic strands, and the moving member may be a secondary tube within the main tubing. The tubing or liner, or both, may carry a metal element for use as an X-ray marker. A smooth plastic nose cone is carried by the distal end of the main tubing, the nose cone being openable to permit ejection of the liner from the tubing.

15 Claims, 5 Drawing Figures

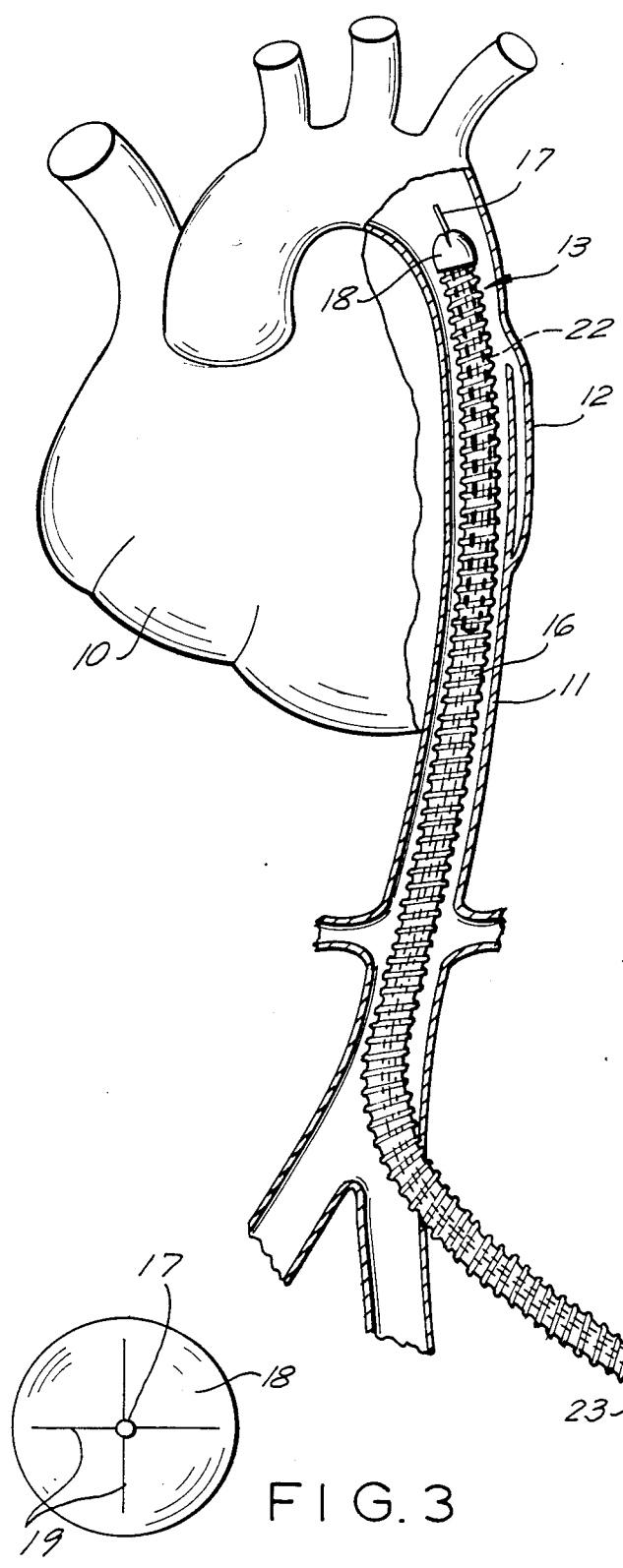
FIG.1
FIG.3
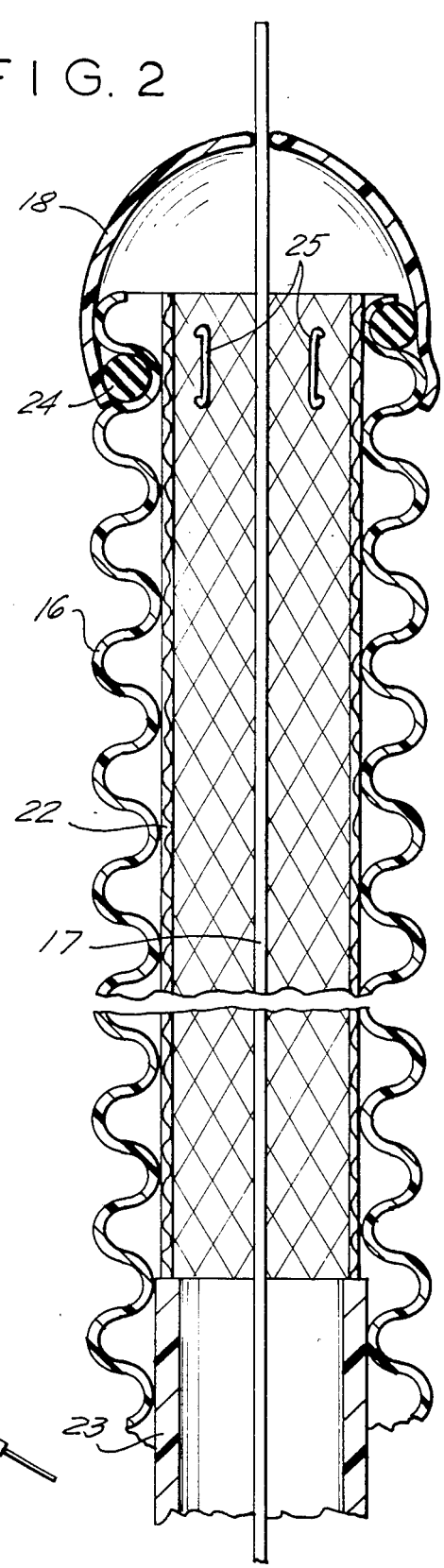
FIG.2

FIG. 4
FIG. 5
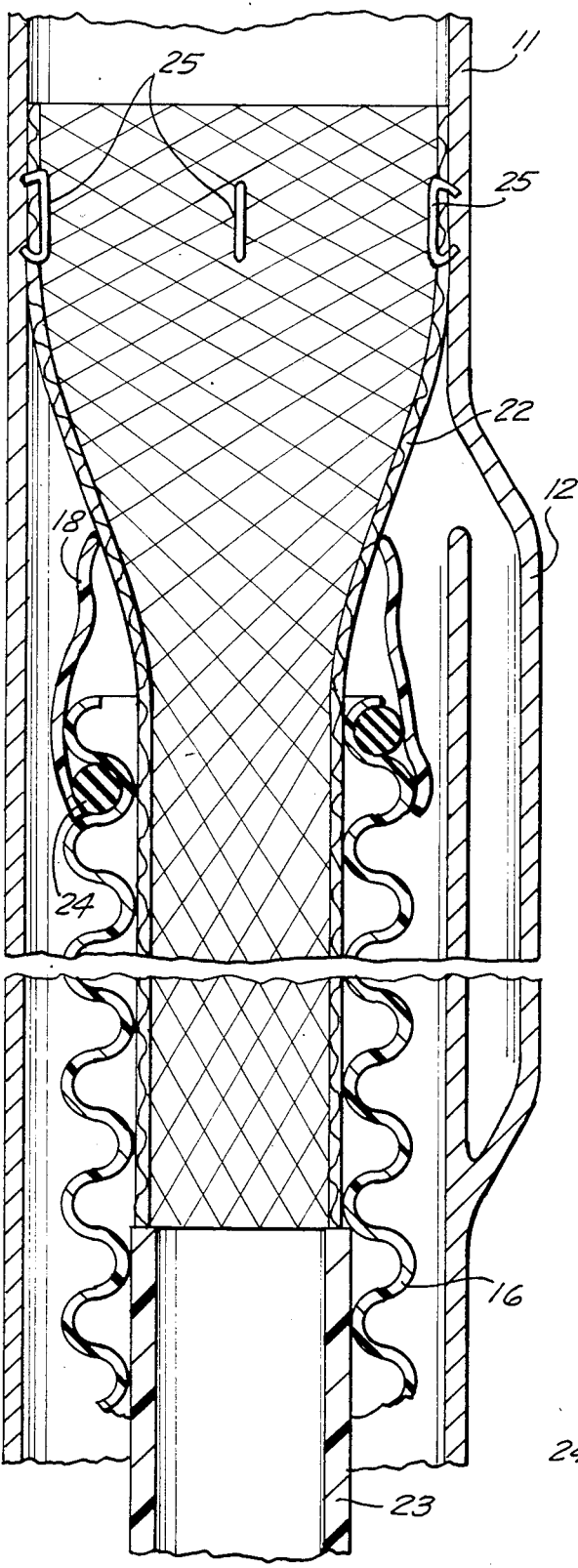
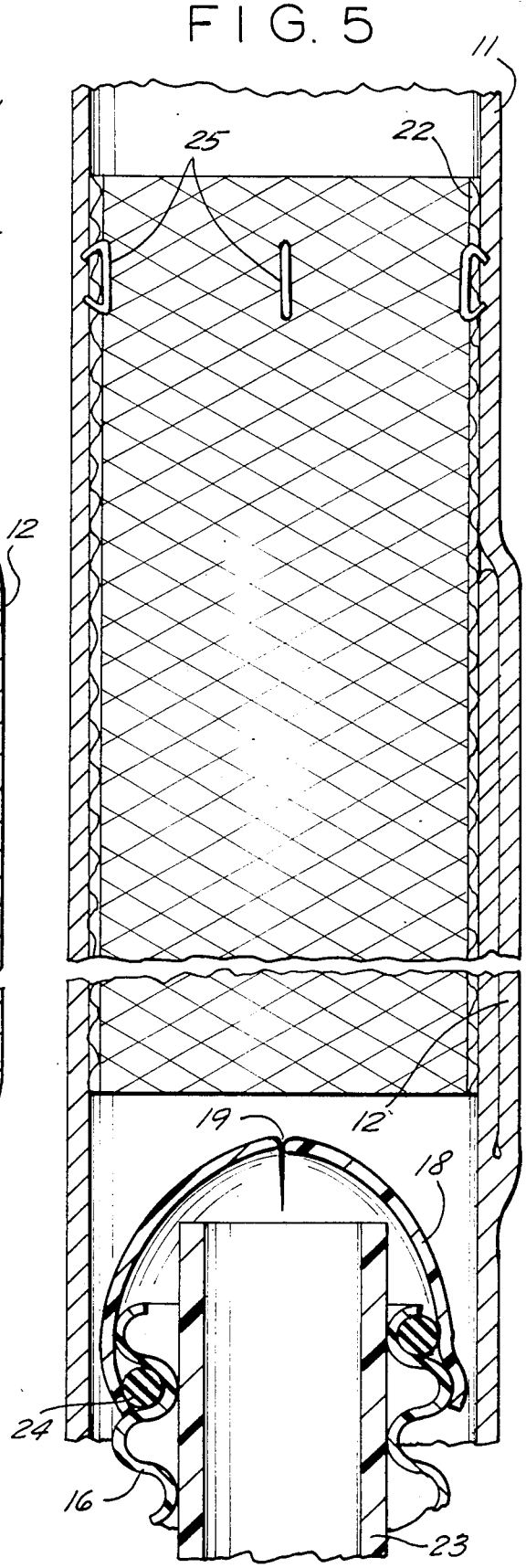

CATHETER ARRANGEMENT HAVING A BLOOD VESSEL LINER, AND METHOD OF USING IT

FIELD OF THE INVENTION

This invention relates to catheters, and more specifically to catheters designed to transport and deploy a liner inside a blood vessel, thus providing means for repair of an afflicted vessel without major surgery.

DESCRIPTION OF PRIOR ART

Catheters, as such, are not new to medical practitioners. They are frequently employed in internal medicine for such purposes as introduction of medications, diagnostics, withdrawal of fluids, recanalization, and many other well known and useful purposes. Several techniques of recanalization and dilatation are known and have been used with various degrees of success. U.S. Pat. No. 4,195,637 describes one particular technique wherein a catheter arrangement incorporating an inflatable balloon at its distal end is inserted into an artery clogged with plaque. The balloon is subsequently inflated to compress the plaque, thus reopening the artery for free flow of blood. Other catheters are used primarily for diagnostic purposes; a radio-opaque dye is introduced through the catheter, and with the aid of an X-ray or a fluoroscope apparatus the anatomical characteristics of the area in question can be studied.

Several different methods for guidance of such catheters are known, these being discussed in U.S. Pat. Nos. 4,033,331 and 3,528,406. In some cases a guide wire is inserted into the artery or canal first, and once in place, the catheter is fitted over the guide wire and is guided to the desired location, whereupon the guide wire is removed and the catheter is then used as intended. Multiple insertions and withdrawals of guide wires and/or catheters can lead to unnecessary complications, e.g., possible start of blood coagulation on the surface of that wire, and other undesirable conditions adversely affecting the patient, including trauma and considerable discomfort. Catheters known at present, although extremely useful in their applications and intended uses, have been of limited value for actual repair of afflicted vessels.

SUMMARY OF INVENTION

The catheter of this invention greatly expands the scope of usage of catheters, simplifies the overall procedures involved in their use, permits both diagnosis and repair, and offers a practical alternative to major surgery. The catheter of this invention is designed to perform several functions. The most important of these involves an expandable tubular liner disposed within the distal end of the catheter in a compressed condition, the liner being transported to a desired position and then ejected from the catheter. Upon ejection, the liner assumes an expanded condition, of a much larger diameter than the catheter, and presses against the inner wall of the artery which is to be treated. In a case where an artery is partially obstructed with plaque, the catheter itself, when entering, enlarges the inside of the artery. The expandable tubular liner, when ejected and placed in position, assumes a larger diameter by virtue of its memory and maintains such opening clear. At the same time, the liner assures that the plaque is contained and no embolism takes place, and that no embolic debris leave the area unintentionally causing possible blockage further downstream.

In a case where an aneurism is to be treated and repaired, again the expandable liner is introduced via the catheter and deployed within the afflicted area. The liner provides a smooth duct for unobstructed and contained flow of blood thereby preventing the blood from entering the area of aneurism. At the same time, it provides a means for reinforcement of the afflicted area, greatly relieving stresses previously imposed on the weak section of the ballooning part of the aneurism. The introduction and deployment of such liner, by means of a catheter, is intended to eliminate or at least minimize the need for otherwise required surgical invasion and repair. Except for the removal of some excess tissue normally associated with such surgery, the same end results can be achieved using the catheter and liner described above. Furthermore, such use causes an infinitely reduced trauma, shock, and discomfort to the patient, and effects a repair at a considerably reduced risk and overall cost.

Normal functions of a catheter, such as introduction of medication or radio-opaque dye for diagnostic purposes, can also be carried out with ease using the present catheter.

The expandable liner is made of suitable biomedical grade of plastic, which is totally compatible with living human tissue. The liner can be given a radio-opaque character by being infused with a suitable filler, such as gold or barrium sulfate, for easy detection and traceability by X-ray during deployments, and also for periodic inspection and evaluation of performance thereafter. The expandable liner is of an open weave braided construction, heat-treated to retain a memory in its fully expanded condition. For transport to the desired location and deployment thereat, the liner is reduced in diameter by compression to fit within the outer tubing of the catheter. The ends of the expandable liner are heat sealed to prevent fraying, and upon deployment, to provide better means for anchoring within the artery.

DESCRIPTION OF THE PREFERRED EMBODIMENT

For purposes of better understanding the principles of this invention reference will be made to the embodiment illustrated in the accompanied drawings. It is to be understood that no limitation of the scope of this invention is hereby implied or intended, and further modifications of this invention could be contemplated by those skilled in the art without departing from the intended purpose.

FIG. 1 is a view, partially in cross-section, showing an aorta afflicted with an aneurism, and a catheter arrangement according to the invention within the aorta;

FIG. 2 is a cross-sectional view, on an enlarged scale, showing the distal end of the catheter arrangement;

FIG. 3 is an end view of the catheter arrangement;

FIG. 4 is a cross-sectional view showing the expandable liner partially deployed within the damaged aorta; and FIG. 5 is a view similar to FIG. 3 showing the expandable liner fully deployed.

Referring now to the drawings, FIG. 1 shows a human heart 10 and an aorta 11, there being an aneurism 12 on the descending part of the aorta. The descending part of a typical aorta has been chosen to show an aneurism and the application of this invention for repairing the aorta. A catheter arrangement 13 chosen to illustrate the present invention is shown extended into the aorta, the distal end of the catheter arrangement being in the vacinity of the aneurism 12.

The catheter arrangement includes (see FIGS. 1 and 2) a main catheter tubing 16, a highly flexible guide wire 17 centrally disposed within tubing 16, and a smooth, flexible nose cone 18 fitted over the very distal end of tubing 16. Main tubing 16 is made of biomedical grade plastic, as are all the other parts of the catheter arrangements, save guide wire 17. The wall of tubing 16 is preferably corrugated to give it torsional resistance while maintaining its longitudinal flexibility.

Nose cone 18 serves two primary functions: first, it provides a soft, smooth tip which prevents injury to the inside of the blood vessel as the catheter is being manipulated and pushed through the blood vessel to the desired location; second, it closes off the distal end of the tubing 16 so as to prevent blood from entering the catheter. As may be seen in FIG. 3, the tip of nose cone 18 is provided with two slits 19, perpendicular to each other, which permit the nose cone to be opened, as will be described below. However, the inherent resilience of the plastic material of which nose cone 18 is formed normally closes the slits.

A flexible, radially expandable, tubular liner 22 is located within the distal end of main tubing 16 (FIGS. 1 and 2). The liner is a tightly woven plastic tube which can be compressed radially from its normal, relatively large diameter (FIG. 5) to a much smaller diameter (FIG. 2), the length of the liner increasing as it is radially compressed. The woven criss-crossed plastic strands of which the liner is made extend at about a 45° angle to the axis of the liner. This bias orientation of the strands, together with their plastic memory, gives the liner its radial resilience. In its compressed condition, liner 22 fits within tubing 16. In this way, main tubing 16 carries liner 22 to the desired location within the blood vessel.

Extending through main tubing 16, and terminating just behind liner 22, is a secondary tube 23. Tube 23 fits loosely within tubing 16 and is slidable longitudinally with respect to tubing 16. The far end of tube 23 abuts against the near end of liner 22, as may be seen in FIG. 2. Tube 23 serves to hold liner 22 in position as main tubing is withdrawn at the time the liner is deployed. A metal ring 24 encircles tubing 16 near its distal end. The ring serves as an X-ray marker, to facilitate fluroscopic observation of the catheter as it is being inserted into the aorta 11. Alternatively, or in addition, metal staples 25 may be carried by liner 22 to serve as X-ray markers. Use of staples has the additional advantage that the ends of the staples, projecting outwardly of liner 22, help to anchor the liner to the interior of the blood vessel in which the liner is deployed.

In use, the catheter arrangement, including main tubing 16 having nose cone 18 mounted on its end and containing liner 22 and tube 23, is inserted into aorta 11 (FIG. 1) by fitting it over the previously-inserted guide wire 17. The catheter is pushed along the guide wire 17 and the aorta until the portion of tubing 17 containing liner 22 is adjacent to the dissection and aneurism 12. Use of X-ray markers 24 and/or 25 aid in determining when this location is reached. Guide wire 17 is then pulled out of tubing 16.

Next, while holding tube 23 against movement, main tubing 16 is withdrawn. As a result, tubing 16 and nose cone 18 slide off liner 22, as shown in FIG. 4, the slits 19 in the nose cone opening to permit the liner to pass through the nose cone. Liner 22 is restrained against radial expansion while it is captured within tubing 16. However, as tubing 16 is pulled off liner 22, axial movement of the liner being restrained by its abutment with the end of tube 23, the liner immediately springs outwardly toward its original larger diameter; this action is illustrated in FIG. 4. Once tubing 16 is pulled off the full length of liner 22, the entire liner is expanded (FIG. 5) and presses against the inner surface of the aorta 11. If staples 25 are employed, they grip the aorta to help anchor the liner in place. Tubing 16 and tube 23 are then completely withdrawn from the aorta.

The fully deployed liner 22, shown in FIG. 5, lines the aorta in the region of aneurism 12. Consequently, blood flow now takes place through the liner, and is prevented from entering the dissection and aneurism. As a result, the aneurism has receded, and the aorta is effectively repaired. It will be appreciated that the repair has been effected without resort to major surgery. Preferably, the liner employed is just long enough to cover the dissection and aneurism.

Although the invention has been described with reference of an aneurism, it has other uses as well. For example, where a blood vessel is partially occluded, movement of the catheter arrangement through the occlusion will enlarge the blood flow path by compressing the material causing the occlusion against the blood vessel wall. The expanded liner introduced at that point will keep the occlusion-causing material compressed and thereby prevent it from thickening and again occluding the vessel. Another use for this invention is one of prophylaxis to prevent heart attacks which are caused by narrowing of the coronary artery. An expandable liner 22 can be deployed within a coronary artery before an occlusion occurs, as a result of plaque build-up, so as to prevent dangerous narrowing of the coronary artery.

I claim:

1. A catheter arrangement comprising:
   a main flexible tubing for insertion into a blood vessel,
   a resilient liner within the tubing, the liner being maintained in a radially compressed condition by the tubing and having a tendency to spring radially outwardly, and the liner being an open weave tube of criss-crossed strands, the tube being devoid of any obstruction to free passage of liquid and solids through the openings in the weave, and
   means for producing relative movement between the liner and tubing, while the tubing is located within a blood vessel, so that the liner escapes from the tubing and expands against the blood vessel wall.

2. A catheter arrangement as defined in claim 1 wherein the liner is a tube of woven plastic strands.

3. A catheter arrangement as defined in claim 2 wherein the strands are criss-crossed and extend at an angle of about 45° with respect to the axis of the liner.

4. A catheter arrangement as defined in claim 1 including a metal member carried by the liner, the member having a portion extending radially outwardly of the liner for engagement with the blood vessel, to anchor the liner to the blood vessel.

5. A catheter arrangement as defined in claim 4 wherein the metal member is a staple.

6. A catheter arrangement as defined in claim 1 wherein the liner carries a radio-opaque material.

7. A catheter arrangement as defined in claim 1 wherein the main tubing is corrugated.

8. A catheter arrangement as defined in claim 1 including a smooth nose cone mounted on the distal end of the main tubing, the nose cone closing that end of the tubing.

9. A catheter arrangement as defined in claim 8 wherein the nose cone has means for opening it to permit the liner to pass through the nose cone and escape from the tubing.

10. A catheter arrangement as defined in claim 8 wherein the means for opening the nose cone are slits in the nose cone, the nose cone being formed of a resilient material which normally closes the slits.

11. A catheter arrangement as defined in claim 1 including a metal member carried by the main tubing.

12. A catheter arrangement as defined in claim 1 wherein the relative movement producing means includes an elongated flexible member located within the main tubing, one end of the member abutting an end of the liner.

13. A catheter arrangement as defined in claim 12 wherein the member is a tube.

14. A catheter arrangement as defined in claim 13 including a flexible guide wire extending through the tube and liner.

15. A method of treating an afflicted blood vessel, comprising the steps of:
  providing a resilient liner in the form of an open weave tube of criss-crossed strands,
  radially compressing the liner, while maintaining its criss-crossed strand structure, and introducing the compressed liner into a length of tubing, the tubing maintaining the liner in its compressed condition against the tendency of the liner to expand radially outwardly,
  inserting into the blood vessel the length of tubing containing the radially expandable liner,
  moving the tubing along the blood vessel to bring the liner adjacent to the point of afflication,
  ejecting the liner from the tubing so that the liner expands radially outwardly to engage the wall of the blood vessel, and
  leaving the liner permanently within the blood vessel.

* * * * *